United States Patent

Yoon

Patent Number: 5,752,970
Date of Patent: May 19, 1998

[54] CANNULA WITH DISTAL END VALVE

[76] Inventor: InBae Yoon, 2101 Highland Ridge Dr., Phoenix, Md. 21131

[21] Appl. No.: 710,506

[22] Filed: Sep. 18, 1996

Related U.S. Application Data

[63] Continuation of Ser. No. 383,520, Feb. 3, 1995, abandoned.

[51] Int. Cl.⁶ .................................................. A61B 17/34
[52] U.S. Cl. .......................... 606/185; 604/167; 604/169
[58] Field of Search ............................ 606/185; 604/15, 604/167, 169, 264, 278; 128/749

[56] References Cited

U.S. PATENT DOCUMENTS

| | | |
|---|---|---|
| 3,721,229 | 3/1973 | Panzer . |
| 4,023,559 | 5/1977 | Gaskell ............................ 604/158 |
| 4,650,459 | 3/1987 | Sheldon . |
| 4,681,110 | 7/1987 | Wiktor ............................ 606/194 |
| 4,850,969 | 7/1989 | Jackson ............................ 604/96 |
| 4,899,729 | 2/1990 | Gill et al. . |
| 5,085,636 | 2/1992 | Burns . |
| 5,114,407 | 5/1992 | Burbank . |
| 5,122,122 | 6/1992 | Allgood ............................ 604/174 |
| 5,197,955 | 3/1993 | Stephens et al. ............................ 604/167 |
| 5,242,412 | 9/1993 | Blake, III ............................ 604/167 |
| 5,300,047 | 4/1994 | Beurrier . |
| 5,318,532 | 6/1994 | Frasssica . |
| 5,320,611 | 6/1994 | Bonutti et al. . |
| 5,334,164 | 8/1994 | Guy et al. . |
| 5,336,203 | 8/1994 | Goldhardt et al. . |
| 5,350,362 | 9/1994 | Stouder, Jr. . |
| 5,350,364 | 9/1994 | Stephens et al. . |
| 5,350,393 | 9/1994 | Yoon . |
| 5,354,280 | 10/1994 | Haber et al. . |
| 5,360,403 | 11/1994 | Mische . |
| 5,360,417 | 11/1994 | Gravener et al. . |
| 5,366,478 | 11/1994 | Brinkerhoff et al. . |

*Primary Examiner*—Michael Buiz
*Assistant Examiner*—Patrick W. Rasche

[57] ABSTRACT

A cannula for introducing medical instruments into an anatomical cavity includes an elongate tubular body defining a lumen and a valve protruding distally from the tubular body for preventing fluid flow through the lumen when medical instruments are withdrawn from the anatomical cavity into the tubular body. The valves are preferably configured as one-way valves such that external forces and pressures exerted on the valves from outside the cannula will not cause the valves to open. The valves can form rounded or blunt distal ends when closed or can be configured in a manner to penetrate anatomical tissue when closed. Furthermore, spring members can be embedded in the valves to provide reinforcement and to bias the valves to a closed condition.

28 Claims, 6 Drawing Sheets

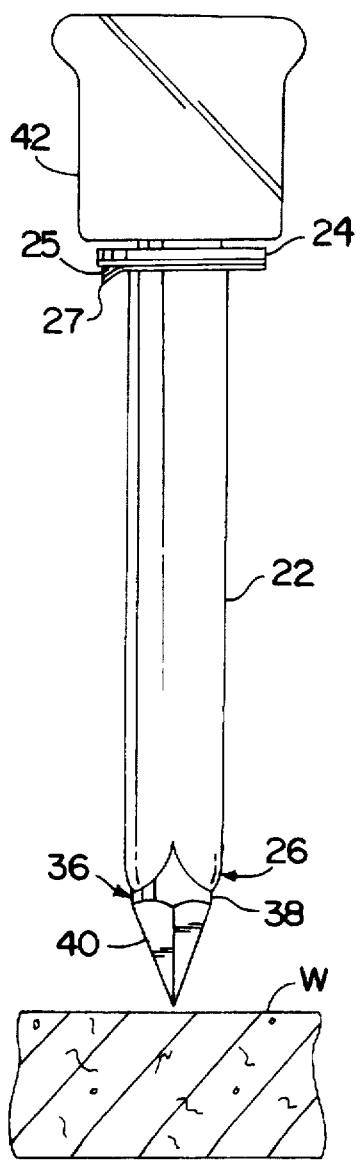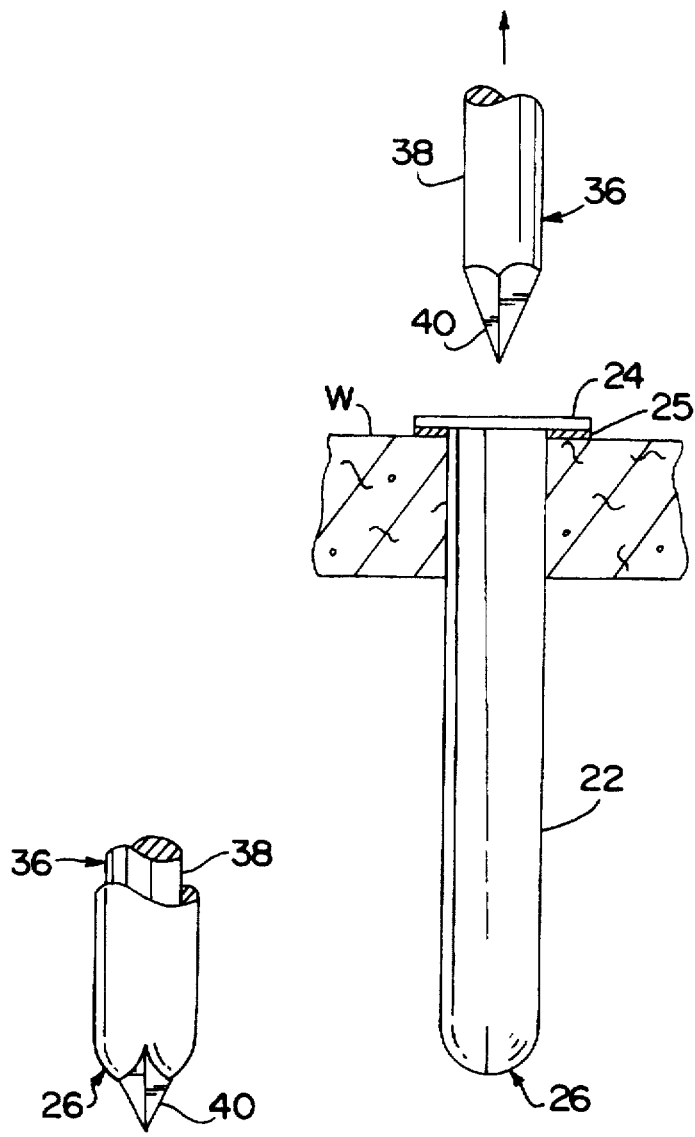
FIG. 3
FIG. 3A
FIG. 4

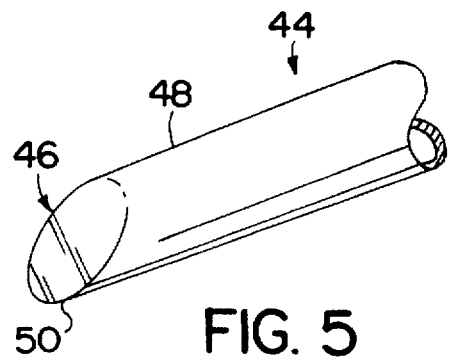
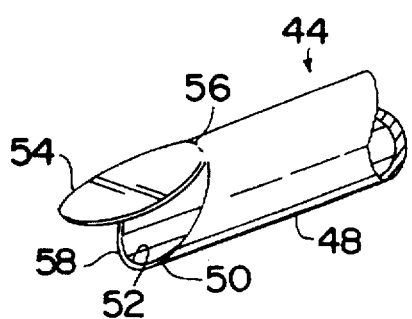
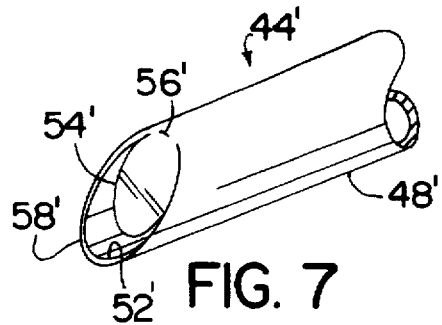
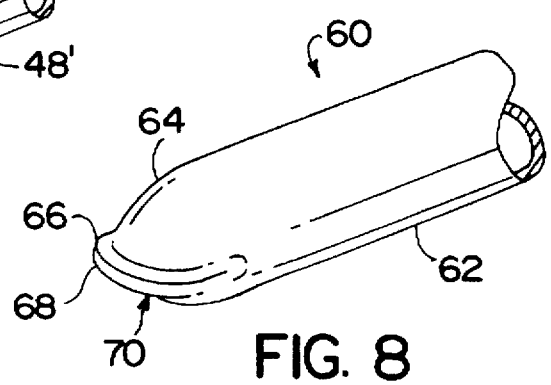
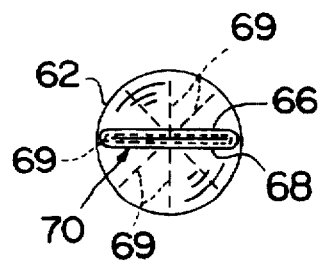

CANNULA WITH DISTAL END VALVE

This application is a continuation of patent application Ser. No. 08/383,520, filed Feb. 3, 1995 abandoned.

BACKGROUND OF THE INVENTION

1. Field of the Invention

The present invention pertains to medical instruments and, more particularly, to a cannula having a valve at a distal end that allows a medical instrument to be inserted into an anatomical cavity through the cannula and prevents the flow of fluids to and from the anatomical cavity when the medical instrument is removed from the cannula.

2. Description of the Prior Art

Medical procedures involving the placement of a cannula, such as a portal sleeve or catheter, through an anatomical cavity wall to provide a passage for insertion of medical instruments frequently require that the passage be sealed to prevent the flow of fluids through the cannula. For example, many medical procedures gain access to an anatomical cavity by utilizing a penetrating member, such as a trocar, obturator or needle, fitted within the cannula such that a sharp tip of the penetrating member protrudes from the cannula for puncturing the cavity wall to establish communication with the interior of the anatomical cavity. The penetrating member is then withdrawn and the cannula left in situ for utilization as a portal to introduce medical instruments into the anatomical cavity. Because it is necessary to prevent fluid flow to and from the site within the anatomical cavity, the cannula must be sealed prior to and subsequent to the introduction of any instruments and while such instruments are in place.

Furthermore, fluids, such as gaseous phase carbon dioxide or nitrous oxide, may be introduced into the anatomical cavity for insufflation as part of the procedure, and the escape of the gas must be prevented during penetration and during the endoscopic procedure. Typically, medical instruments are inserted into the cannula via a valve housing mounted externally of the anatomical cavity wall at the proximal end of the cannula. The valve housing is provided with a valve, such as a flapper valve, that allows a medical instrument to be inserted into the cannula. The valve prevents the flow of fluids to and from the anatomical cavity and closes when the medical instrument is removed from the cannula.

A disadvantage of prior art cannulae with valve housings is that the valve housings can protrude from the patient's body, complicating the operating theater space and increasing the length of medical instruments inserted through the cannulae during medical procedures. Moreover, the valve housings usually have only a single, particular size passage dependent upon the penetrating member. However, other medical instruments to be introduced into the anatomical cavity through the passage may be of diverse types and sizes and it will be appreciated that fluid can escape past smaller instruments.

SUMMARY OF THE INVENTION

Accordingly, it is a primary object of the present invention to overcome the above mentioned disadvantages of the prior art and to improve cannulae of the type used to create a portal through the wall of an anatomical cavity by incorporating a valve at the distal end of a cannula to prevent fluid flow through the cannula when medical instruments are withdrawn from the cannula.

Another object of the present invention is to minimize portions of a cannula disposed externally of an anatomical cavity wall while preventing the flow of fluids through the cannula when medical instruments are withdrawn.

A further object of the present invention is to bias a valve to a normally closed position at the distal end of a cannula and to permit medical instruments to be introduced through the cannula while preventing fluid flow or leakage around the instruments.

The present invention has another object in the use of valve members at the distal end of a cannula to produce a sealing relation with medical instruments of various sizes.

Some of the advantages of the present invention over the prior art are that the cannula can be used without external valve housings, that medical instruments of various shapes and sizes can be passed through the cannula without significant fluid flow or leakage through the cannula, that medical instruments having sharp tips can be inserted through the cannula without damaging the valve, that the cannula can be split longitudinally to accommodate medical instruments of various sizes and to remove objects larger than the penetrating member used to place the cannula in the wall of an anatomical cavity, that the distal end of the cannula can be configured to form a blunt or rounded tip for increased safety or a sharp tip for penetrating anatomical tissue, that the cannula can be used with standard trocars, safety shielded trocars and retractable and/or protruding safety penetrating instruments to more fully protect the penetrating tips of the instruments, and that the cannula can be inexpensively manufactured to be economically disposable for single patient use or sterilizable for reuse.

The present invention is generally characterized in a cannula for introducing medical instruments into an anatomical cavity including an elongate tubular body defining a lumen and a valve protruding distally from the tubular body for preventing fluid flow through the lumen when medical instruments are withdrawn from the anatomical cavity into the tubular body.

Another aspect of the present invention is generally characterized in a cannula for introducing medical instruments into an anatomical cavity comprising an elongate tubular body defining a lumen and sealing means protruding distally from the tubular body for engaging medical instruments to prevent fluid flow through the lumen when the medical instruments are inserted into the anatomical cavity.

Yet another aspect of the present invention is generally characterized in a method of forming a portal in the wall of an anatomical cavity including the steps of fitting a penetrating member within a cannula so that a tip of the penetrating member protrudes distally from a distal end of the cannula, penetrating the anatomical cavity wall with the tip of the penetrating member, moving at least one of the penetrating member and the cannula relative to one another such that the tip of the penetrating member is proximally spaced from the distal end of the cannula, and closing a valve disposed at the distal end of the cannula.

Other objects and advantages of the present invention will become apparent from the following description of the preferred embodiments taken in conjunction with the accompanying drawings wherein, unless specified otherwise, like parts or parts that perform like functions are identified in each of several figures by the same reference numerals.

BRIEF DESCRIPTION OF THE DRAWINGS

FIGS. 3, 3A and 4 are side views, partly in section, illustrating use of the cannula of FIG. 1.

FIG. 5 is a fragmentary view, in perspective, of a modified cannula according to the present invention in a closed state.

FIG. 6 is a fragmentary view, in perspective, of the cannula of FIG. 5 in an open state.

FIG. 7 is a fragmentary view, in perspective, of a modification of the cannula of FIG. 5.

FIG. 8 is a fragmentary perspective view of another cannula according to the present invention.

FIG. 9 is a frontal view of the cannula of FIG. 8.

DESCRIPTION OF THE PREFERRED EMBODIMENTS

The cannula of the present invention can be utilized to provide access to any type of anatomical cavity; and, accordingly, while the cannula is described hereinafter for use as a portal sleeve in endoscopic procedures, such as laparoscopy, it will be appreciated that the cannula can also be used as a catheter, needle, safety shield or other tubular component of a medical instrument to provide access to small cavities, such as veins and arteries, as well as large cavities, such as the abdomen.

Figure 1:
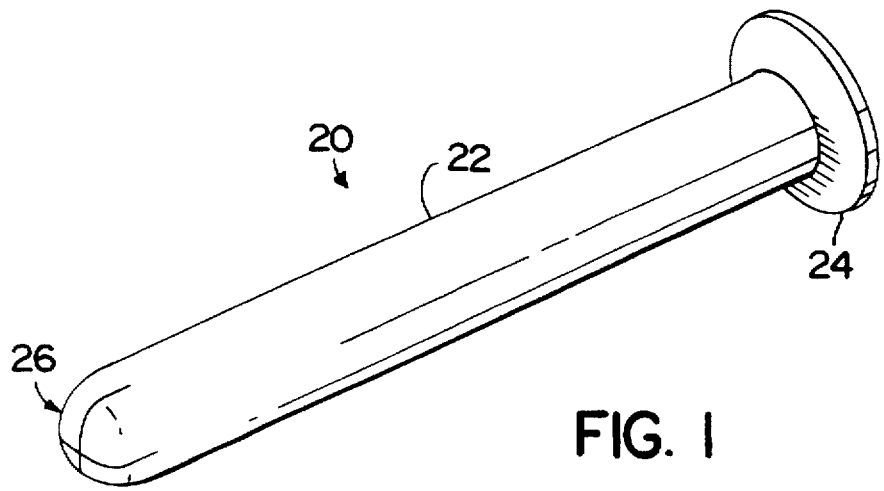
FIG. 1 is a perspective view of a cannula according to the present invention.
Figure 2:
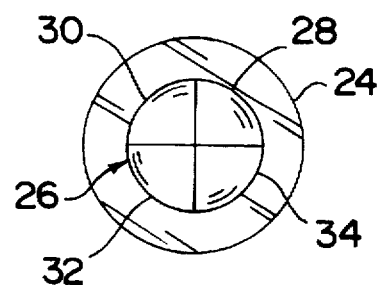
FIGS. 2 is a frontal view of the cannula of FIG. 1.

A cannula 20 according to the present invention, as illustrated in FIGS. 1 and 2, includes an elongate tubular body 22 with a round flange 24 at a proximal end and a valve or seal 26 at a distal end. Tubular body 22 can have any desirable configuration in cross-section, including cylindrical or tubular configurations, in accordance with the procedure to be performed and the anatomical cavity to be penetrated. Preferably, the tubular body 22 is made of a substantially cylindrical length of rigid or flexible material, such as stainless steel or other medically acceptable plastic or metal material, and has a tubular configuration defining a lumen between the proximal and distal ends for introducing medical instruments through the cannula.

Flange 24 forms an annular ring around the open proximal end of the tubular body 22 and is suitably dimensioned to prevent the cannula from being pushed through the wall of the anatomical cavity. The flange can also provide a surface for attaching the cannula to the anatomical cavity wall. In FIG. 3, for example, a thin layer of medical adhesive 25 is carried on the distal face of the flange 24 for engaging an anatomical cavity wall to bond with the cannula. The adhesive 25 is backed by a covering 27 which can be peeled away from the adhesive or otherwise removed to expose the adhesive prior to use.

Referring again to FIGS. 1 and 2, valve 26 is formed at the distal end of the tubular body 22 and includes four valve members or flaps 28, 30, 32 and 34 normally biased to a closed state when no instrument is passed through the cannula. Flaps 28, 30, 32 and 34 each have a generally spherical triangular shape to sealingly mate with one another when closed and to form a hemispherical or rounded wall closing the distal end of the tubular body 22. The flaps are preferably made of relatively flexible medical grade materials, such as certain elastomeric materials, that can substantially conform to the shape of medical instruments passed through the cannula and return to a closed state sealing the distal end of the cannula when the instruments are removed. If the tubular body of the cannula is made of the same material as the valve, the valve and tubular body can be formed as an integral one-piece unit as shown. Alternatively, the valve and tubular body of the cannula can be made of different materials and joined together using conventional techniques, such as bonding, to form an integral unit.

In use, cannula 20 will normally be placed in the wall of an anatomical cavity using a penetrating member, such as a trocar 36, disposed within the tubular body 22 of the cannula as shown in FIG. 3. Trocar 36 is conventional and includes a cylindrical shaft 38 having a tissue penetrating distal end or tip 40 that protrudes distally from the tubular body 22 of the cannula when the trocar is fitted within the cannula. The trocar 36 can be fitted within the cannula 20 by grasping the hub 42 at the proximal end of the trocar and positioning the tip 40 of the trocar in the open proximal end of the cannula. The trocar 36 is then advanced through the cannula 20 by moving the hub 42 distally relative to the cannula until the tip 40 and/or cylindrical shaft 38 of the trocar forces flaps 28, 30, 32 and 34 apart, opening the valve and permitting the tissue penetrating tip 40 of the trocar to protrude distally from the cannula. Tip 40 can be distally spaced from the flaps of the valve 26 so that the valve flaps engage the cylindrical shaft 38 of the trocar 36, as shown in FIG. 3, or the trocar can be disposed within the cannula as shown in FIG. 3A so that the valve flaps engage the tapered sides of the tip 40. Hub 42 at the proximal end of the trocar can also function as a stop by engaging flange 24 of the cannula when the tip of the trocar protrudes to prevent further distal movement of the trocar relative to the cannula and to urge the cannula to move with the trocar when the tip of the trocar is advanced distally through anatomical tissue.

With trocar 36 fitted within cannula 20, an anatomical cavity wall W can be penetrated by positioning the tissue penetrating tip 40 of the trocar 36 against the wall W and moving the hub 42 distally in the direction of the wall. The tissue penetrating tip 40 at the distal end of the trocar 36 is thus pushed into the anatomical wall W creating an opening. Cannula 20 is forced into the opening created by the trocar and is moved distally through the anatomical cavity wall W with the trocar 36 until flange 24 abuts an external surface of the anatomical wall W, as shown in FIG. 4, preventing further distal movement of the cannula through the wall. Trocar 36 can then be retracted or withdrawn from the anatomical cavity as shown, leaving the cannula 20 in place within the anatomical cavity wall W to function as a valved portal for introduction of medical instruments into the anatomical cavity. Withdrawal of trocar 36 also permits flaps 28, 30, 32 and 34 to return to the closed state where peripheral edges of the flaps are seated against one another to seal the distal end of the cannula. Depending on the type of tissue and the size of the opening through which the cannula is inserted, cannula 20 can be held in place by frictional engagement of the tubular body with the wall of the anatomical cavity and/or by use of a medical adhesive, tape, sutures or any other medically acceptable method of attachment.

Medical instruments, such as endoscopes and tubes connected to fluid sources, can be passed through the cannula to access the anatomical cavity and, when the instruments separate the flaps of the valve at the distal end of the cannula, the resilience of the flaps will tend to close the flaps against the instruments thereby helping to maintain a seal preventing fluid flow around the instruments. In the case of instruments that fit telescopically within the cannula, a seal is normally maintained along the length of the instruments such that the flaps need not seal against the instruments.

The cannula of the present invention can be modified as illustrated in FIGS. 5 and 6 so that the distal end of the modified cannula 44 forms a flapper valve 46. The modified cannula 44 includes a tubular body 48 having a beveled distal end 50 defining an elliptical opening 52 with an elliptical valve member or flap 54 normally disposed over the opening and biased to a closed state sealing the distal end of the tubular body. Flap 54 includes an integral hinge 56 at a proximal end connecting the flap with a trailing edge of opening 52, and the flap 54 is biased about the hinge 56 in a counterclockwise direction, looking at FIG. 6, into sealing engagement with a peripheral edge 58 of the distal end opening.

Cannula 44 can be placed in the wall of an anatomical cavity using a penetrating member disposed within the tubular body 48 as described above for cannula 20 or the beveled distal end 50 of the cannula can be configured for use as a tissue penetrating tip so that the cannula can be inserted into anatomical tissue without the need of having to utilize a separate penetrating member. When the distal end of the cannula is used as a tissue penetrating tip, the force from tissue contact on flap 54 will maintain the flap in a seated condition against the beveled opening of the cannula closing the valve and preventing fluid flow through the cannula during penetration. Once the cannula is positioned in the wall of the anatomical cavity, the valve at the end of the cannula can be opened by passing instruments through the tubular body until flap 54 is pivoted away from the distal opening 52.

FIG. 7 illustrates a modification of the cannula shown in FIG. 5. The modified cannula 44' is similar to cannula 44 but with a valve flap 54' configured to pivot part way into the tubular body 48'. Flap 54' is biased to pivot about hinge 56' in a counterclockwise direction, looking at FIG. 7, to a closed position where the flap is angularly spaced from the distal end opening 52'. The flap 54' fits snugly within the tubular body 48' in the closed position to form a seal preventing the flow of fluid through the cannula when any medical instruments are removed.

FIGS. 8 and 9 illustrate another modification of the cannula according to the present invention wherein the modified cannula 60 includes a tubular body 62 similar to tubular body 22 and a valve 70 having a rounded distal end 64 like valve 26 but split longitudinally to form a pair of jaws 66 and 68 in opposed relation. Jaws 66 and 68 resemble puckered lips and are normally biased together to form a seal at the distal end of the cannula. Valve 70 can be opened by passing instruments through the tubular body and using the distal ends of the instruments to pry open the jaws. The jaws can be flexible to conform to the shape of the instruments or rigid to form predetermined size openings. The rounded end 64 of the valve is configured to accommodate opening of the jaws, for example by resiliently deforming or collapsing against the tubular body like a bellows. Accordingly, the rounded end of the valve is preferably made of a resilient material that will bias the jaws together in sealing relation while permitting the jaws to be separated by instruments advanced distally through the cannula. Alternatively, or in addition to making the rounded end of the valve of resilient materials, separate spring members can be embedded within the rounded end and/or the jaws, as shown in phantom at 69 in FIG. 9, to bias the jaws together.

Figure 10:
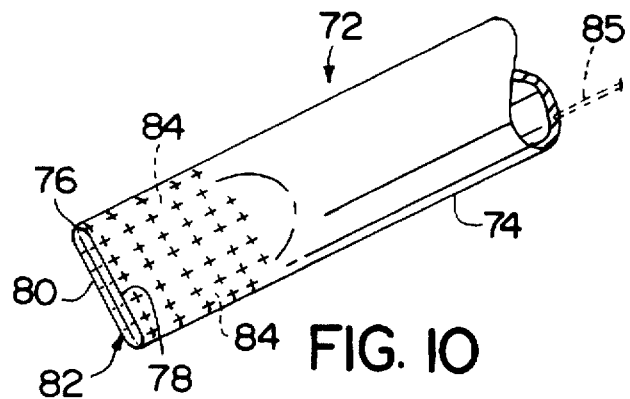
FIG. 10 is a fragmentary perspective view of yet another modified cannula according to the present invention.

FIG. 10 illustrates another modification of the cannula of the present invention wherein the modified cannula 72 includes a tubular body 74 like those described above but with a flattened distal end 76 having laterally opposed sides 78 and 80 biased together in sealing relation to form a valve or seal 82. A plurality of spaced spring members 84 are embedded or otherwise mounted at the distal end of the tubular body and are appropriately oriented, for example in lateral and longitudinal directions as shown, to bias the laterally opposed sides of the distal end of the tubular body to a flattened condition. The laterally opposed sides 78 and 80 of the valve 82 normally contact one another across the width of the tubular body 74 to form a seal closing the distal end of the tubular body when no instruments are passed through the cannula. Alternatively, or in addition to using spring members 84, a passage can be formed longitudinally alongside or through the cylindrical wall of the tubular body 74, as shown in phantom at 85, for communicating with an expandable membrane at the distal end 76 of the tubular body 74 to seal the distal end.

Figure 11:
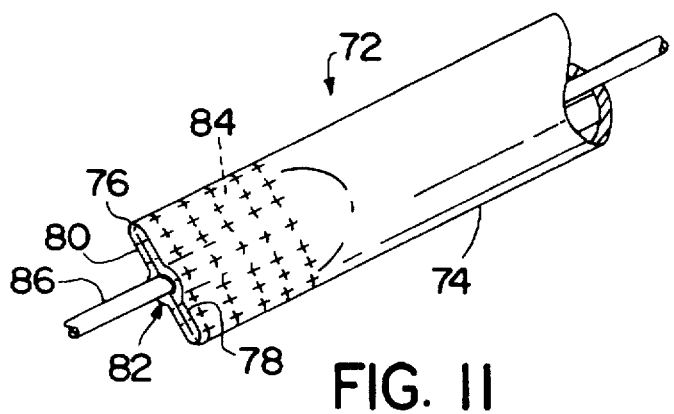
FIG. 11 is a fragmentary perspective view of the cannula of FIG. 10 with a small diameter instrument inserted through the cannula.
Figure 12:
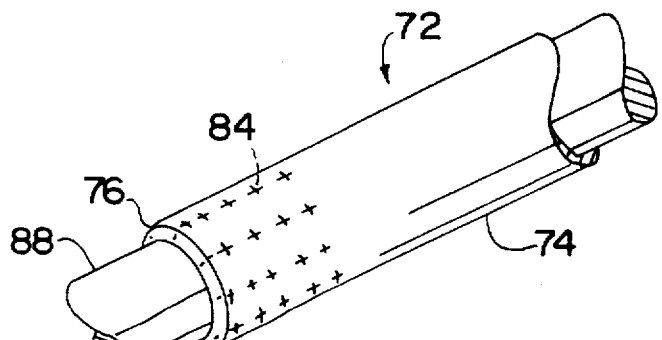
FIG. 12 is a fragmentary perspective view of the cannula of FIG. 10 with a large diameter instrument inserted through the cannula.

In use, cannula 72 can accommodate instruments of various size and shape because of the resilient nature of the valve 82. For example, when an instrument 86 of smaller diameter than the tubular body 74 is passed through the cannula 72 as shown in FIG. 11, opposed sides 78 and 80 of the valve 82 can be resiliently separated by the instrument to permit passage of the instrument through the valve, and the sides of the valve will conform to the shape of the instrument thereby maintaining a seal. In the case of an instrument 88 that fits telescopically within the tubular body of the cannula, valve 82 can expand to a generally cylindrical shape as shown in FIG. 12 to permit passage of the instrument while maintaining a seal along its length.

Figure 13:
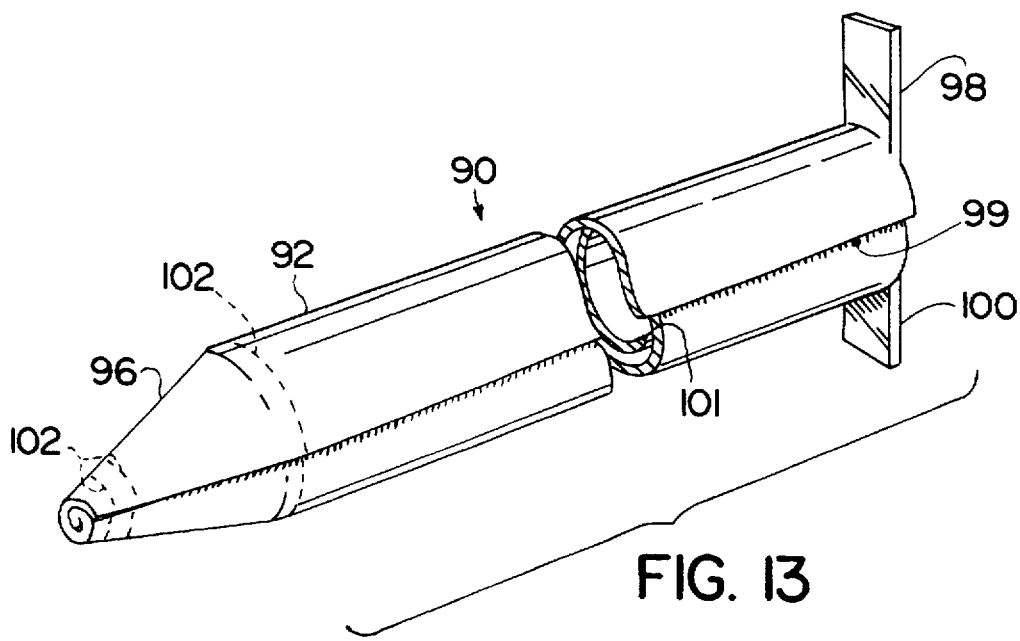
FIG. 13 is a perspective view of yet another modified cannula according to the present invention.

The modified cannula 90 shown in FIG. 13 includes an involuted tubular body 92 formed of a resilient material rolled into a spiral and a valve 94 formed at the distal end of a resilient involuted cone 96 extending from the rolled distal edge of the tubular body. Flanges 98 and 100 extend transversely from angularly spaced locations along the rolled proximal edge of the tubular body to prevent the cannula from being pushed through the wall of an anatomical cavity and to provide surfaces for attaching the cannula to the anatomical cavity wall. Flange 98 is connected near an outer lateral edge 99 of the tubular body and flange 100 is connected near an inner lateral edge 101 so that the flanges can be rotated relative to one another to roll or unroll the tubular body. Also, edge 99 of the tubular body can be smooth as shown or configured to form a cutting edge, if desired.

The involuted overlapping surfaces of the tubular body 92 and cone 96 are preferably in sliding contact with one another to maintain a seal along the length of the cannula and are biased into the spiral shapes shown, for example by fabricating the tubular body and cone or resilient materials and/or by using embedded circular spring members 102 spaced longitudinally along the length of the cone and/or the tubular body of the cannula. Valve 94 at the distal end of the cone 96 is formed by mating contact between the rolled distal edges of the cone and is normally closed to form a seal.

Figure 14:
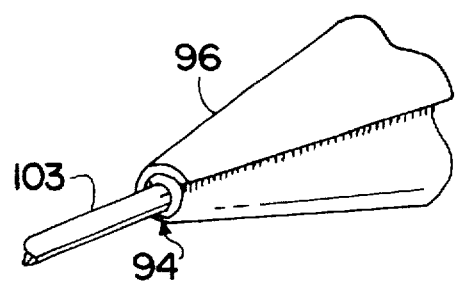
FIG. 14 is a fragmentary perspective view of an instrument being passed through the cannula of FIG. 13.

In use, when an instrument 103 is inserted into the cannula 90 as shown in FIG. 14, the tubular body 92 and cone 96 can resiliently unfurl to increase the size of the lumen in order to accommodate the instrument. Thus, when the instrument contacts the cone 96, the walls of the cone will tend to unfurl until valve 94 at the distal end of the cone is opened creating an aperture through which the instrument can pass. The tubular body and cone can be made of resilient materials and/or spring biased to a coiled condition such that the valve will tend to close against the instrument forming a seal.

It will also be appreciated that the expandable nature of cannula 90 facilitates removal of objects from the anatomical cavity that would normally be larger than the instruments used to retrieve the objects. For example, when an object is grasped using a medical instrument, such as a forceps, and it is desired that the object be withdrawn from the anatomical cavity, the tubular body 92 can be unfurled to increase the size of the lumen so that the object can pass through the tubular body. The size of the lumen can be controlled by sliding a larger tubular instrument over the forceps until it contacts the cone 96 of the cannula causing the cone, and thus the tubular body, to unfurl. Alternatively, flanges 98 and 100 at the proximal end of the tubular body can be rotated relative to one another to unfurl the tubular body and cone of the cannula. The object can then be drawn through the cone and into the cylindrical portion while the valve 94 closes behind the object.

Figure 15:
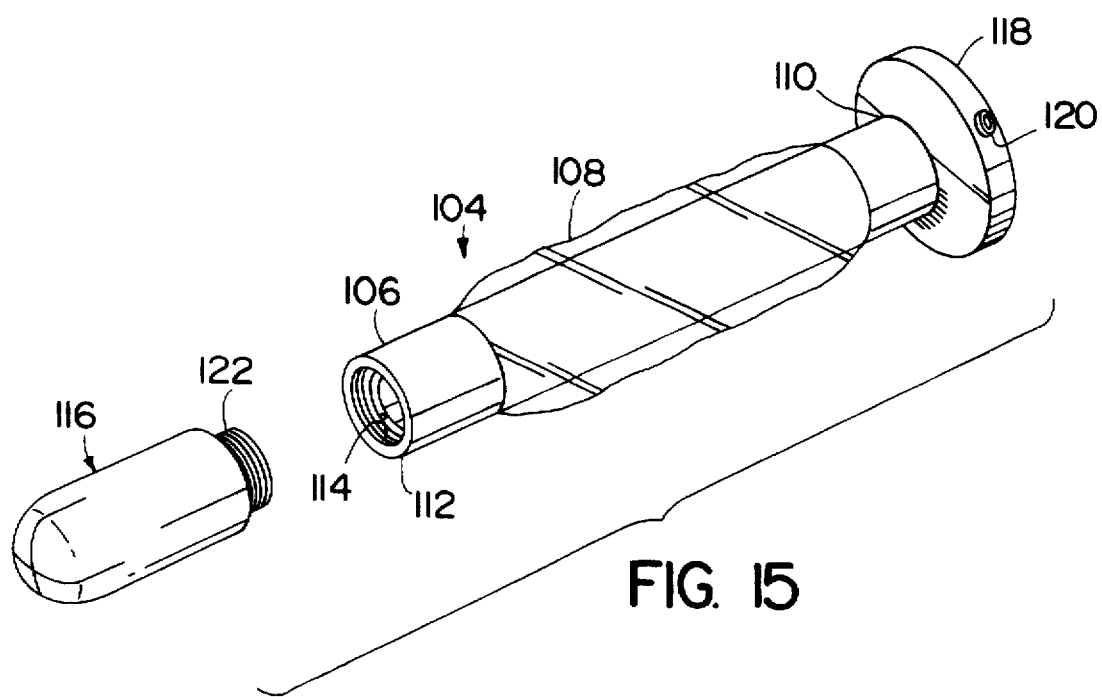
FIG. 15 is an exploded perspective view of still another modification of the cannula according to the present invention.

Another modification of the cannula according to the present invention is illustrated in FIG. 15. The modified cannula 104 includes a tubular body 106 similar to tubular body 22 but with a distensible membrane 108 mounted intermediate proximal and distal ends 110 and 112 of the tubular body and a threaded recess 114 formed at the distal end for threadedly mating with a detachable valve 116. A flange 118 is mounted at the proximal end 110 of the tubular body and is similar to flange 24 with the exception of mounting a valve 120 for communicating fluids to and from the distensible membrane 108. Detachable valve 116 is similar to valve 26 but includes a threaded cylindrical portion 122 at a proximal end for threadedly engaging the distal end 112 of the tubular body 106. In use, a detachable valve, such as valve 116, is chosen by the user and attached to the tubular body 106 of the cannula prior to placing the cannula in the wall of an anatomical cavity. If the cannula is to be fitted within a relatively large opening, such as a laparotomy formed as part of a so-called "minilap" procedure, the membrane 108 can be distended by connecting a fluid source with valve 120 and expanding the membrane to fill the space between the tubular body and the walls of the opening in order to maintain a proper fit and seal. Valve 116 operates like valve 26; however, any of the valves previously described can be configured to be detachable from the tubular body of the cannula.

From the above, it will be appreciated that the cannula of the present invention can be used in any type of anatomical tissue to provide a valved passage or portal without the need of an external valve housing. Any type of valve can be carried or formed at the distal end of the cannula so long as the valves are normally closed when no instruments are passed through the cannula. The valves are preferably configured as one-way valves such that external forces and pressures exerted on the valves from outside the cannula will not cause the valves to open. Any of the valves shown and described herein can be configured in a manner to form relatively smooth convex surfaces or to penetrate anatomical tissue when closed. Also, the valves can be formed with the tubular bodies as an integral one-piece unit or the valves can be formed as separate units and connected with the tubular bodies by threaded engagement, bonding, hinged connection or any other suitable means of attachment. Furthermore, spring members, like spring members 84, can be embedded in any of the valves and in any orientation relative to a longitudinal axis of the cannula to provide reinforcement and to bias the valves to a closed condition.

It will also be appreciated that the cannula of the present invention can be used for engaging medical instruments of various sizes in sealing relation to prevent fluid flow around the instruments while allowing the medical instruments to be introduced into an anatomical cavity and removed in succession during a procedure. The cannula of the present invention can be used in combination with known valve housings if desired but is particularly advantageous when used alone in order to minimize external structures and to reduce the overall size of the portal.

Depending on the type of tissue and the size of the opening through which the cannula is inserted, the cannula can be held in place or anchored by frictional engagement of the tubular body with the wall of the anatomical cavity, medical adhesives, tape, sutures or any other medically acceptable method of attachment. In the case of sutures, the flange can be formed with one or more circumferentially spaced apertures or eyelets to facilitate passage of the suture material through the flange and into the anatomical tissue. The cannula can also be anchored by use of one or more tissue penetrating members carried by the cannula, as disclosed in Applicant's copending patent application, Ser. No. 08/243,493, filed May 15, 1994, the disclosure of which is incorporated herein by reference.

When a distensible membrane is provided, it can be placed anywhere on the tubular body and can be a flaccid, bag-like membrane as shown or an elastic membrane that conforms closely to the exterior shape of the tubular body in the deflated or unexpanded condition. Furthermore, any number of membranes can be positioned on the tubular member and communicated with a single, common valve or multiple valves as desired.

The cannula of the present invention is also advantageous when used with penetrating instruments of the type that move penetrating components relative to one another to protect tissue penetrating tips of the instruments upon entering an anatomical cavity. For example, the cannula of the present invention could be used with penetrating instruments having retractable penetrating members, such as those disclosed in U.S. Pat. Nos. 5,330,432; 5,324,268; 5,320,610; 5,336,176; and 5,360,405 to Yoon and Applicant's pending applications Ser. No. 07/848,838, filed Mar. 10, 1992; Ser. No. 07/845,177, filed Sep. 15, 1992; Ser. No. 07/945,177, filed Sep. 15, 1992; Ser. No. 08/079,586, filed Jun. 22, 1993; Ser. No. 08/195,512, filed Feb. 14, 1994; Ser. No. 08/196,029, filed Feb. 14, 1994; Ser. No. 08/196,027, filed Feb. 14, 1994; Ser. No. 08/195,178, filed Feb. 14, 1994; Ser. No. 08/237,734, filed May 4, 1994; Ser. No. 08/247,205, filed May 20, 1994; Ser. No. 08/254,007, filed Jun. 3, 1994; and Ser. No. 08/260,439, filed Jun. 15, 1994; the disclosures of which are incorporated herein by reference. The cannula of the present invention could also be used with penetrating instruments of the type that can move the cannula and/or a safety member, such as a shield or probe, distally relative to the penetrating member upon penetrating into an anatomical cavity, such as those disclosed in Applicant's pending patent applications Ser. No. 08/083,220, Jun. 24, 1993; Ser. No. 08/083,728, filed Jun. 29, 1993; Ser. No. 08/115,152, filed Sep. 2, 1993; Ser. No. 08/300,535, filed Sep. 6, 1994; Ser. No. 08/301,897, filed Sep. 7, 1994; Ser. No. 08/315,506, filed Sep. 30, 1994; Ser. No. 08/316,335, filed Sep. 30, 1994;

Ser. No. 08/317,939, filed Oct. 4, 1994; Ser. No. 08/327,686, filed Oct. 24, 1994; and Ser. No. 08/362,222, filed Dec. 23, 1994; the disclosures of which are incorporated herein by reference. Other penetrating instruments that can be utilized with the cannula of the present invention to retract a penetrating member while causing the cannula and/or a safety member such as a shield or probe to protrude are disclosed in Applicant's pending applications Ser. Nos. 08/279,170 and 08/279,172, filed Jul. 22, 1994, the disclosures of which are incorporated herein by reference. When the cannula of the present invention is used with a penetrating instrument that permits relative movement between the cannula and a penetrating member such that the tip of the penetrating member is proximally spaced from the distal end of the cannula, it will be appreciated that the valve at the distal end of the cannula can be made to close around the penetrating member, providing enhanced safety and that any housings mounting the cannula can be configured to be detached from the cannula once the cannula is placed in the wall of the anatomical cavity.

The components of the cannula can be made of any suitable, medical grade materials to permit sterilization for reuse or for single patient use and can be made of multiple parts of various configurations and materials to reduce cost. The features of the various embodiments described above can be combined in any manner desired dependent upon the procedural requirements and the complexity of the cannula.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. In combination, a cannula for establishing a passage through an anatomical cavity wall to permit insertion of medical instruments into the anatomical cavity and a penetrating member disposed in said cannula and having a proximal end mounted by a hub and a sharp distal end for penetrating anatomical tissue, said cannula comprising an elongate tubular body defining a lumen and having a proximal end for placement outside the anatomical cavity and a distal end for placement within the anatomical cavity, and a valve protruding distally from said distal end of said tubular body, wherein said tubular body is substantially longer than said valve and said tubular body length is such that said distal end of said penetrating member protrudes from said valve when said penetrating member hub abuts said proximal end of said tubular body, and wherein said valve is normally biased to a closed state preventing fluid flow through said lumen when said penetrating member is withdrawn from said cannula and no medical instruments are inserted into the anatomical cavity through said tubular body.

2. A combination as recited in claim 1 wherein said valve includes a tubular distal end biased to a flattened condition where opposed surfaces of said flattened distal end are held together in sealing relation.

3. A combination as recited in claim 2 and further comprising spring members for biasing said opposed surfaces of said flattened distal end together in sealing relation.

4. A combination as recited in claim 1 wherein said tubular body is formed by an involuted cylindrical wall rolled into a spiral and said valve is defined by rolled distal edges of an involuted conical wall extending distally from said involuted cylindrical wall.

5. A combination as recited in claim 4 wherein said involuted cylindrical wall defines said lumen and further comprising at least two handles extending from inner and outer overlapping proximal edges, respectively, of said rolled cylindrical wall for unfurling said involuted cylindrical wall of said tubular body to selectively increase the size of said lumen.

6. A combination as recited in claim 4 wherein an outer lateral edge of said cylindrical wall is configured as a cutting edge.

7. A combination as recited in claim 1 wherein said tubular body and said valve are formed as an integral one-piece unit.

8. A combination as recited in claim 1 and further comprising means for anchoring said tubular body in the anatomical cavity wall.

9. A combination as recited in claim 8 wherein said means for anchoring said tubular body includes a flange extending transversely from a proximal end of said tubular body.

10. In combination, a cannula for establishing a passage through an anatomical cavity wall to permit insertion of medical instruments into the anatomical cavity and a penetrating member disposed in said cannula and having a proximal and mounted by a hub and a sharp distal end for penetrating anatomical tissue, said cannula comprising an elongate tubular body defining a lumen and having a proximal end for placement outside the anatomical cavity and a distal end for placement within the anatomical cavity, and a valve protruding distally from said distal end of said tubular body, said tubular body having a length permitting said distal end of said penetrating member to protrude from said valve when said penetrating a member hub abuts said proximal end of said tubular body, said valve being normally biased to a closed state preventing fluid flow through said lumen when said penetrating member is withdrawn from said cannula and no medical instruments are inserted into the anatomical cavity through said tubular body;

wherein said valve defines a substantially smooth convex surface when preventing fluid flow through said lumen.

11. A combination as recited in claim 10 wherein said valve includes a pair of opposed jaws biased together in sealing relation, said jaws being formed on opposite sides of a longitudinal slit formed in said convex surface.

12. A combination as recited in claim 10 wherein said valve includes plural flaps biased to close against one another.

13. A combination as recited in claim 12 wherein said flaps are spherical triangles and said substantially smooth convex surface is hemispherical.

14. In combination, a cannula for establishing a passage through an anatomical cavity wall to permit insertion of medical instruments into the anatomical cavity and a penetrating member disposed in said cannula and having a proximal end mounted by a hub and a sharp distal end for penetrating anatomical tissue, said cannula comprising an elongate tubular body defining a lumen and having a proximal end for placement outside the anatomical cavity and a distal end for placement within the anatomical cavity, and a valve protruding distally from said distal end of said tubular body, said tubular body having a length permitting said distal end of said penetrating member to protrude from said valve when said penetrating member hub abuts said proximal end of said tubular body, said valve being normally biased to a closed state preventing fluid flow through said lumen when said penetrating member is withdrawn from said cannula and no medical instruments are inserted into the anatomical cavity through said tubular body;

wherein said valve includes a flap pivotally mounted at a distal end of said tubular member and biased to a closed position against said distal end of said tubular member.

15. A combination as recited in claim 14 wherein said distal end of said tubular member is beveled and said flap is elliptical.

16. In combination, a cannula for establishing a passage through an anatomical cavity wall to permit insertion of medical instruments into the anatomical cavity and a penetrating member disposed in said cannula and having a proximal end mounted by a hub and a sharp distal end for penetrating anatomical tissue, said cannula comprising an elongate tubular body defining a lumen and having a proximal end for placement outside the anatomical cavity and a distal end for placement within the anatomical cavity, and a valve protruding distally from said distal end of said tubular body, said tubular body having a length permitting said distal end of said penetrating member to protrude from said valve when said penetrating member hub abuts said proximal end of said tubular body, said valve being normally biased to a closed state preventing fluid flow through said lumen when said penetrating member is withdrawn from said cannula and no medical instruments are inserted into the anatomical cavity through said tubular body;

wherein said valve is made of an elastic material reinforced by spring members.

17. In combination, a cannula for establishing a passage through an anatomical cavity wall to permit insertion of medical instruments into the anatomical cavity and a penetrating member disposed in said cannula and having a proximal end mounted by a hub and a sharp distal end for penetrating anatomical tissue, said cannula comprising an elongate tubular body defining a lumen and having a proximal end for placement outside the anatomical cavity and a distal end for placement within the anatomical cavity, and a valve protruding distally from said distal end of said tubular body, said tubular body having a length permitting said distal end of said penetrating member to protrude from said valve when said penetrating member hub abuts said proximal end of said tubular body, said valve being normally biased to a closed state preventing fluid flow through said lumen when said penetrating member is withdrawn from said cannula and no medical instruments are inserted into the anatomical cavity through said tubular body;

wherein said tubular body and said valve are formed separately and further comprising means for detachably coupling said valve with said tubular body.

18. In combination, a cannula for establishing a passage through an anatomical cavity wall to permit insertion of medical instruments into the anatomical cavity and a penetrating member disposed in said cannula and having a proximal end mounted by a hub and a sharp distal end for penetrating anatomical tissue said cannula comprising an elongate tubular body defining a lumen and having a proximal end for placement outside the anatomical cavity and a distal end for placement within the anatomical cavity, and a valve protruding distally from said distal end of said tubular body, said tubular body having a length permitting said distal end of said penetrating member to protrude from said valve when said penetrating member hub abuts said proximal end of said tubular body, said valve being normally biased to a closed state preventing fluid flow through said lumen when said penetrating member is withdrawn from said cannula and no medical instruments are inserted into the anatomical cavity through said tubular body;

and further comprising a membrane disposed around said tubular member and means for expanding said membrane.

19. In combination, a cannula for establishing a passage through an anatomical cavity wall to permit insertion of medical instruments into the anatomical cavity and a penetrating member disposed in said cannula and having a proximal end mounted by a hub and a sharp distal end for penetrating anatomical tissue, said cannula comprising an elongate tubular body defining a lumen and having a proximal end for placement outside the anatomical cavity and a distal end for placement within the anatomical cavity, and a seal protruding distally from said distal end of said tubular body, wherein said tubular body is substantially longer than said seal and said tubular body length is such that said distal end of said penetrating member protrudes from said seal when said penetrating member hub abuts said proximal end of said tubular body, and wherein said seal engage said penetrating member and medical instruments inserted through said cannula after said penetrating member is withdrawn to prevent fluid flow through said lumen when the penetrating member and medical instruments are inserted into the anatomical cavity through said cannula.

20. A combination as recited in claim 19 wherein said seal includes plural flaps biased to close against one another.

21. A combination as recited in claim 19 wherein said seal includes a pair of opposed jaws biased together in sealing relation, said jaws being flexible to conform to the shape of medical instruments.

22. A combination as recited in claim 19 wherein said seal includes a tubular distal end biased to a flattened condition where opposed surfaces of said flattened distal end are held together in sealing relation.

23. A combination as recited in claim 19 wherein said tubular body is formed by an involuted cylindrical wall rolled into a spiral and said seal is defined by rolled distal edges of an involuted conical wall extending distally from said involuted cylindrical wall.

24. A method of forming a portal in the wall of an anatomical cavity comprising the steps of fitting a penetrating member within a cannula so that a sharp tip of the penetrating member protrudes distally from a distal end of the cannula;

using the sharp tip of the penetrating member to create an opening in the anatomical cavity wall;

advancing the penetrating member and the cannula through the opening created in the anatomical cavity wall;

moving at least one of the penetrating member and the cannula relative to one another such that the sharp tip of the penetrating member is proximally spaced from the distal end of the cannula; and closing a valve disposed at the distal end of the cannula.

25. A method as recited in claim 24 wherein said moving step includes the steps of holding the penetrating member in a fixed position and protruding the cannula in a distal direction relative to the penetrating member.

26. A method as recited in claim 24 wherein said moving step includes the steps of holding the cannula in a fixed position and retracting the penetrating member in a proximal direction relative to the cannula.

27. A method as recited in claim 24 wherein said moving step includes the steps of retracting the penetrating member proximally and protruding the cannula distally.

28. A method as recited in claim 24 and further comprising the steps of withdrawing the penetrating member from the cannula and opening the valve by inserting a medical instrument through the cannula.

* * * * *